United States Patent [19]
Agarwala et al.

[11] Patent Number: 6,041,259
[45] Date of Patent: Mar. 21, 2000

[54] EXTERNALLY WORN MEDICAL DEVICE

[75] Inventors: Poonam Agarwala, New Brighton; Andrzej M. Malewicz, New Hope, both of Minn.

[73] Assignee: Empi, Inc., St. Paul, Minn.

[21] Appl. No.: 08/990,080

[22] Filed: Dec. 12, 1997

[51] Int. Cl.[7] .................................................. A61N 1/00
[52] U.S. Cl. ............................................................ 607/46
[58] Field of Search ............................... 607/1–3, 10, 46, 607/48, 58; 600/523; D21/330; D24/185, 186; D14/132

[56] References Cited

U.S. PATENT DOCUMENTS

| | | | |
|---|---|---|---|
| 4,534,063 | 8/1985 | Krumin et al. | |
| 4,917,092 | 4/1990 | Todd et al. | 607/46 |
| 5,003,984 | 4/1991 | Muraki et al. | 600/523 |
| 5,195,517 | 3/1993 | Chen | 607/3 |
| 5,666,273 | 9/1997 | Kurcbart | 361/814 |

*Primary Examiner*—William E. Kamm
*Assistant Examiner*—George R. Evanisko
*Attorney, Agent, or Firm*—Kinney & Lange, P.A.

[57] ABSTRACT

A medical device, such as a TENS unit, includes a case and a cover which are pivotally connected. The cover is attached to a patient's clothing by a clip. When the cover and case are in a closed position, a control panel having a display and inputs is positioned between the case and cover. When a latch is released, the case pivots away from the cover to a first open position in which the control panel is generally horizontal. The patient may view and access the control panel when the device is in the first open position, without having to remove the device from the patient's clothing.

4 Claims, 7 Drawing Sheets

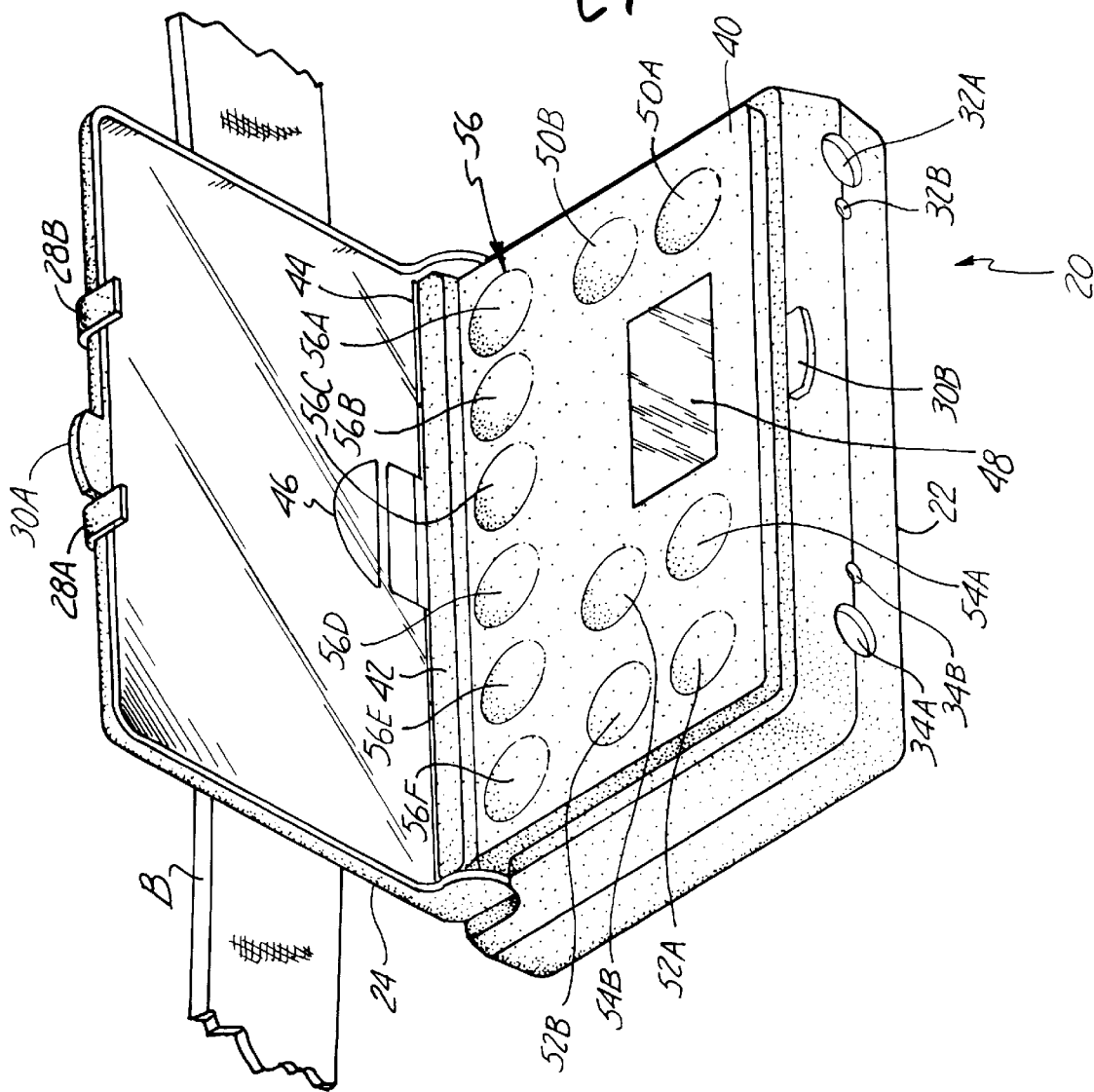

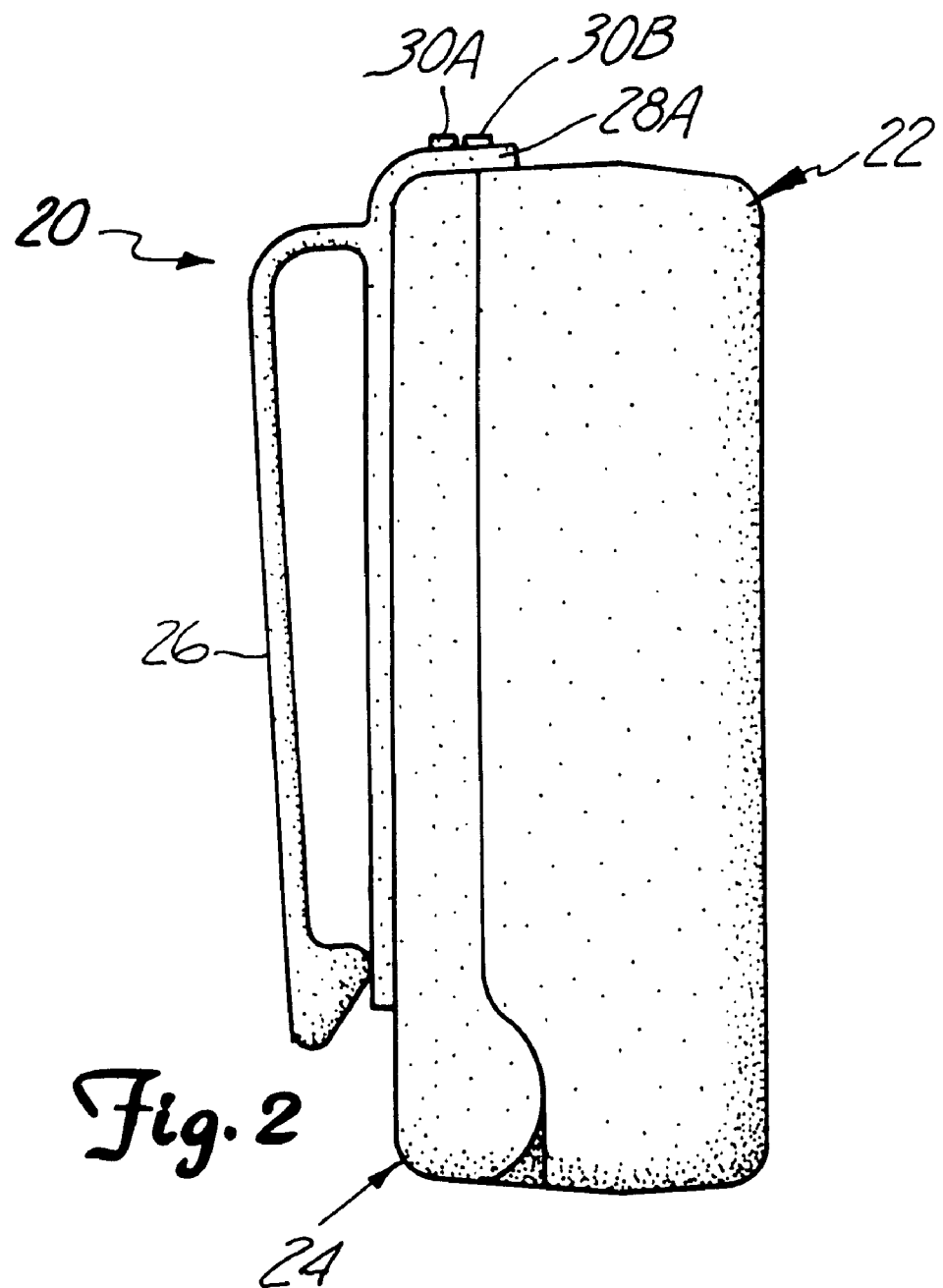

EXTERNALLY WORN MEDICAL DEVICE

BACKGROUND OF THE INVENTION

The present invention relates to a device which is attached to a patient's clothing, and can be opened to allow access to a control panel. More particularly, the present invention relates to a transcutaneous electrical nerve stimulation (TENS) device which is worn by a patient and which allows the patient to control treatment while storing information used to evaluate the effectiveness of the pain treatment.

Millions of people suffer daily from chronic pain. A variety of treatment programs have been developed to alleviate chronic pain. One such program is medicinal pain treatment. Medicinal pain treatments utilize pill or other drug-type forms. An alternative treatment program is transcutaneous electrical nerve stimulation (TENS). A TENS system sends controlled bursts of electrical impulses into muscles and nerves at particular surface points. A mild vibrating sensation is felt by the patient using the TENS system. The pulses induce the patient's nervous system to raise its own natural substances, which prevent pain signals from reaching the brain. A TENS device can be used by a patient numerous times throughout the day whenever a patient desires pain relief.

The various pain treatments have been successful in achieving both short term and long term pain relief. However, since the physiological and psychological aspects of chronic pain are not yet fully understood, validating the effectiveness of any one pain treatment has remained an elusive goal. The need for measuring the outcomes of pain treatment is becoming more apparent.

A clinical outcome measurement usually takes place in a carefully controlled environment in order to reduce the number of variables to a minimum. This type of study is very good at verifying the null hypothesis of the experiment, but the controlled nature of the study may influence the outcome, as this controlled environment may introduce a hidden bias into the experiment. Some of the clinical conditions, such as pain or psychological state of the patient, cannot be measured in objective terms. Pain is the most prevalent complaint of patients and the single most frequent reason a person visits a physician, yet measurement of pain relief, and therefore quantifying treatment effectiveness, poses significant difficulties.

Presently, there are several methods of measuring clinical pain available, such as comparison of the patient's pain with experimentally induced pain and measurement of drug dosage required to abate the pain. The most common method for measuring pain and validating the effectiveness of a pain treatment is the manual pain rating scale. The manual pain rating scale operates independently from the particular pain treatment being used. An example is a Visual Scale which consists of a straight line drawn on a piece of a paper, the ends of which define the extreme limits of the pain experienced. Two other common types of manual pain rating scales are the Verbal Descriptor Scale and the Numeric Pain Scale. The Verbal Descriptor Scale (VDS) consists of a series of adjectives which describe different levels of pain. Alternatively, a Numeric Pain Scale (NPS) uses a series of consecutive numbers (e.g. from 1 to 10) with the smallest number representing "no pain" and the largest number representing "worst pain imaginable".

There are basically two approaches for using manual pain rating scales, absolute and comparative. The absolute approach measures the severity of the pain at a particular point in time. The comparative approach provides a measurement of the change in pain over time. When the patient periodically visits the clinician, the manual pain rating scale test is administered. The clinician provides the manual pain rating scale to the patient who then rates the perceived pain level on the scale provided. The clinician then collects the completed manual pain rating scale for future reference and comparison with other test results.

The manual pain rating scale is devised simply to measure the magnitude or intensity of pain at an arbitrary point in time. The manual pain rating scale may be used in conjunction with a pain treatment in an attempt to gauge the effectiveness of that treatment. However, the manual pain rating scale has a number of inadequacies. First, the manual pain rating scale is used primarily for clinical purposes by a practiced clinician. The form is completed on the periodic occasion when a patient visits his or her clinician. Therefore, records are not kept each and every time the pain treatment is used, rendering any data taken skewed and of limited value. Second, the manual pain rating scale does not "record" the pain level before and after each pain treatment. Third, the manual pain rating scale does not take into account the level of pain treatment being administered. Finally, the manual pain rating scale does not have the ability to store the duration of a pain treatment session.

In addition, where the manual pain rating scale is used at home by the patient, other deficiencies are encountered. These include: (1) "cramming bias, i.e., do all the paperwork at once before the clinic visit, (2) bias from comparison of how the pain was scored in the past, (3) lost data sheets, (4) lack of convenience being a demotivation, (5) disincentive for a clinic to use the tool due to the huge data reduction work load of processing even a few patients, and (6) data errors generated in interpreting paper scales, computer entry errors, and loss of data.

The above-stated inadequacies of the manual pain rating scale greatly impede its ability to provide any meaningful feedback as to the effectiveness of the pain treatment being used. The level of pain being experienced by the patient should be measured before each and every use of the pain treatment to provide an accurate history of the patient. Similarly, the measure of change in pain level following each pain treatment session is required to accurately determine the effectiveness of the treatment. The intensity level of each pain treatment and the length of a pain treatment session are necessary to provide an adequate explanation of the overall effectiveness. Importantly, the pain and pain treatment related data should be stored to create, in effect, a diary documenting a patient's improvement and correlation of the improvement to the pain treatment employed. The manual pain rating scale simply does not have these capabilities.

A substantial need exists for a convenient system having the ability to measure and record a patient's pain level before and after each pain treatment session along with the intensity and length of the pain treatment session.

SUMMARY OF THE INVENTION

The present invention is a medical device which is worn by a patient and which can be viewed and operated without removing the device from the patient's clothing. The device includes a case and a cover which are pivotally connected together. A control panel including a display and a plurality of inputs is mounted on the case. A clip on the cover attaches the cover to a patient's clothing so that the cover is generally vertical.

A latch holds the case in a closed position adjacent the cover so that the control panel is generally vertical and located between the case and cover. When the patient releases the latch, the case is allowed to pivot to a first open position in which the control panel is generally horizontal and is viewable and accessible by the patient. A stop element on the case engages the cover to define the first open position.

BRIEF DESCRIPTION OF THE DRAWINGS

FIGS. 1A–1C are perspective views of a TENS device in a closed position and in first and second open positions, respectively.

FIG. 2 is a side view of the TENS device.

DETAILED DESCRIPTION OF THE PREFERRED EMBODIMENTS

A preferred embodiment of transcutaneous electrical nerve stimulation (TENS) device 20 which includes an electronic pain intensity scale and feedback system is shown in FIGS. 1A–1C, 2 and 3. TENS device 20 includes case 22 and back cover 24. Back cover 24 is clipped to a patient's belt B by belt clip 26 when TENS device 20 is in use by the patient.

Figure 1A:
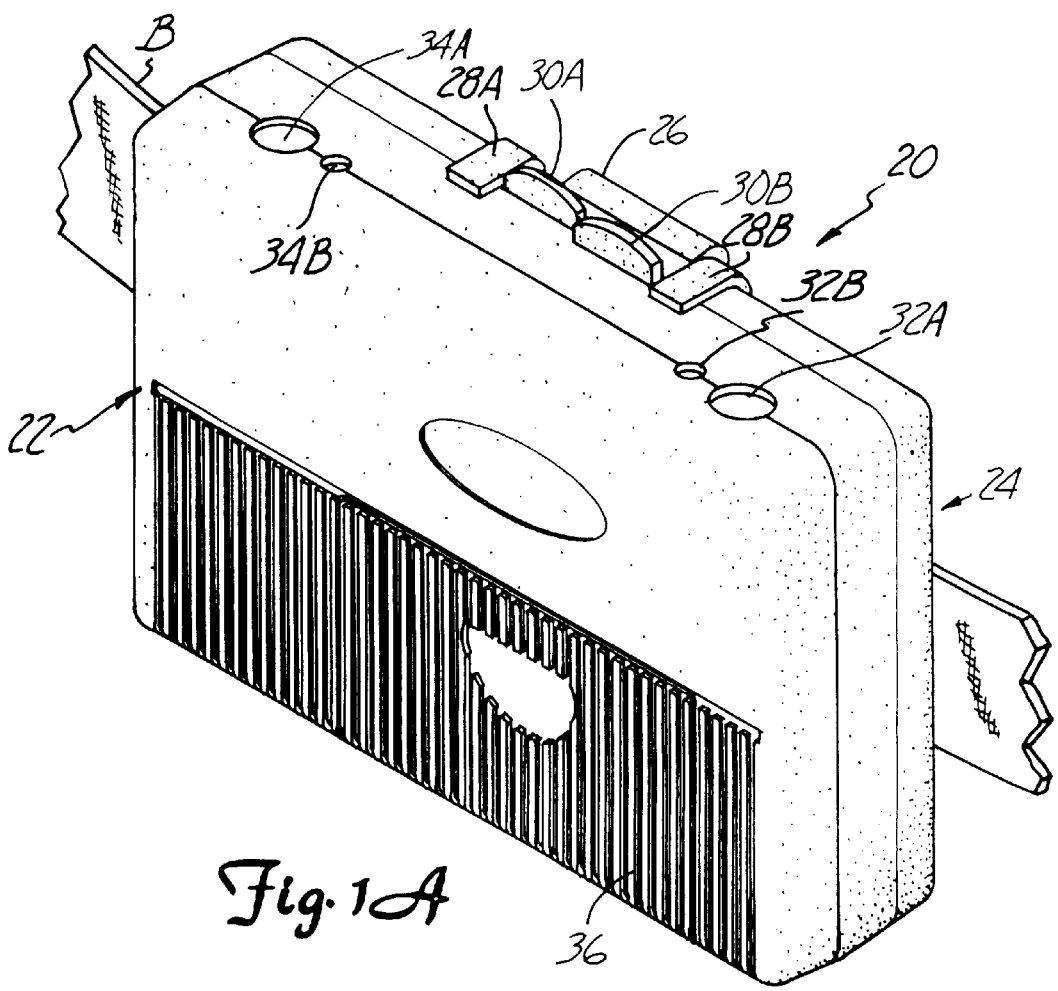

Back cover 24 is pivotally connected to case 22. In FIG. 1A, case 22 and back cover 24 are adjacent one another in a "closed" position. A pair of resilient clips or fingers 28A and 28B extend from the top of back cover 26 and hold case 22 in the closed position. Tab 30A (at the top of back cover 24) and tab 30B (at the top of case 22) are pried apart to release case 22 from fingers 28 and open TENS device 20. In the embodiment shown in FIG. 1A, TENS device 20 provides two output channels ("channel 1" and "channel 2"). Output terminals 32A and 32B are the channel 1 output terminals, while terminals 34A and 34B are the channel 2 output terminals.

TENS device 20 is battery powered. Access to the battery compartment is provided through battery compartment cover 36 on the front side of case 22.

In FIG. 1B, case 22 has been pivoted to a first "open" position, where control panel 40 is accessible for viewing and actuation by the patient. In FIG. 1B, case 22 is oriented at approximately 90° to back cover 24 so that case 22 is generally horizontal. Control panel 40 is oriented so that it can be read and used by the patient when device 20 is mounted on belt B (or a waistband or pocket) and is open as shown in FIG. 1B.

Figure 1C:
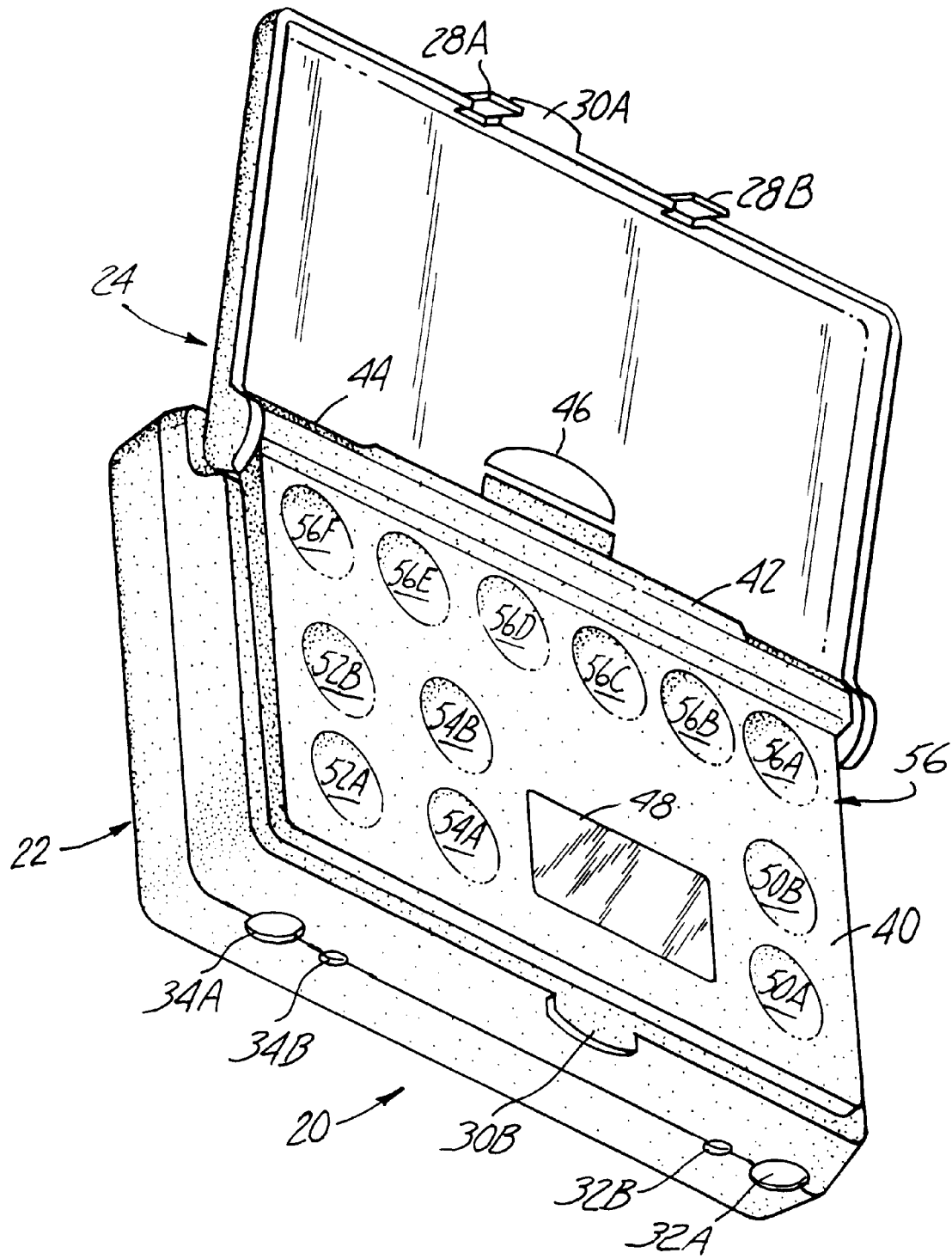

FIG. 1C shows case 22 as it has been pivoted beyond the first open position to a second open position. In this second open position, case 22 and cover 24 are at approximately at 180° to one another. The second open position is particularly useful when TENS device 20 is placed on a flat surface, such as a table.

The first open position (shown in FIG. 1B) is defined by shoulder 42 (FIGS. 1C and 3) on case 22. When tabs 30A and 30B are pried apart to release case 22 from fingers 28, case 22 pivots outward and downward until lower edge 44 of back cover 24 engages shoulder 42.

Back cover 24 is molded plastic, and has sufficient resiliency so that it can be flexed to some extent. By gently pressing on shoulder release region 46 of back cover 24, the patient (or clinician) can flex the center portion of back cover 24 sufficiently to move lower edge 44 out of engagement with shoulder 42. This allows case 22 to continue to pivot downward with respect to back cover 24.

Figure 3:
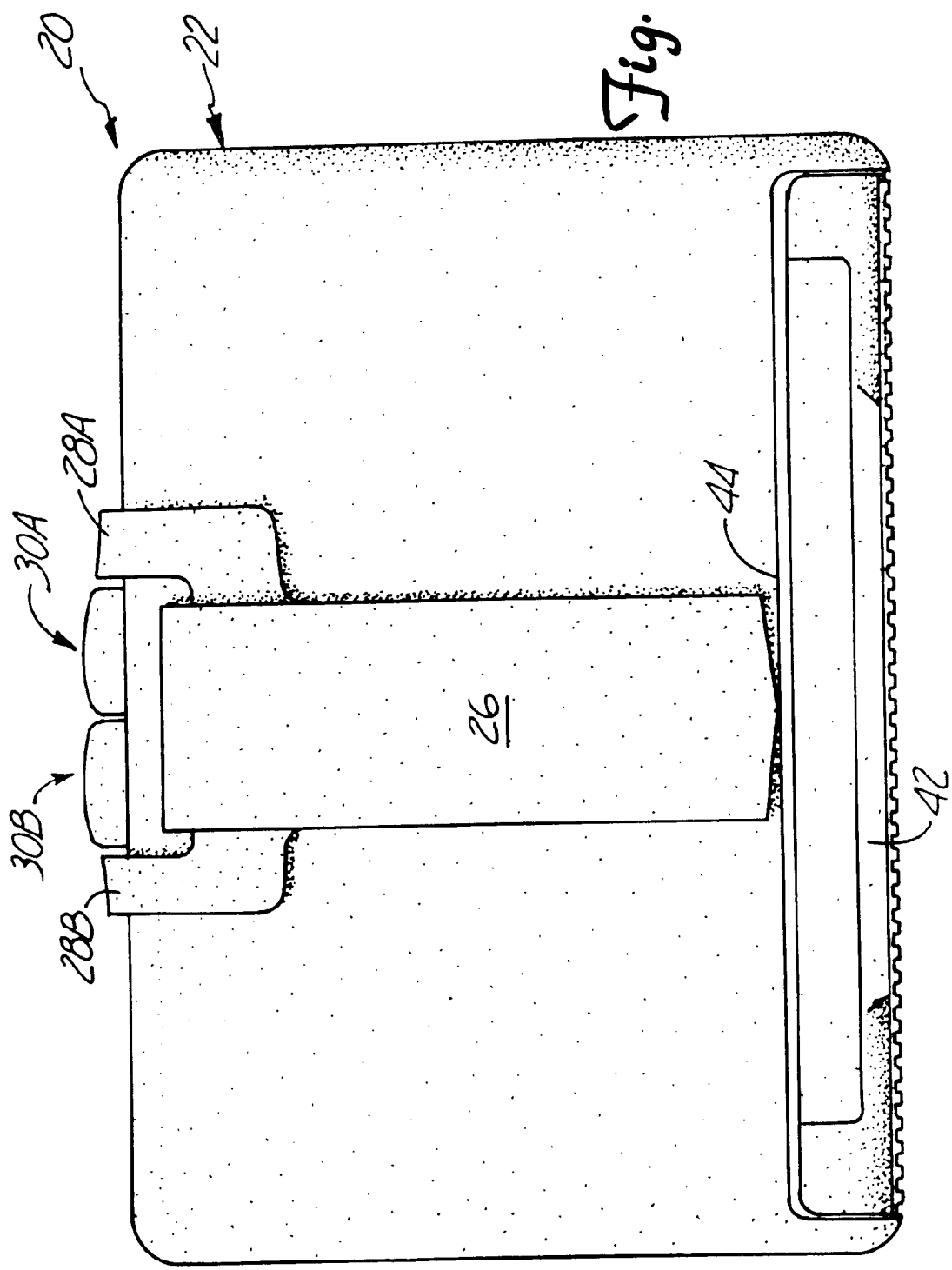
FIG. 3 is a rear view of the TENS device.

As shown in FIG. 1C and FIG. 3, shoulder 42 does not extend the entire width of case 22, but rather is located in a central part. This allows clearance to be achieved between shoulder 42 and the center portion of lower edge 44 of back cover 24 when pivoting case 22 to the second open position illustrated in FIG. 1C.

Figure 4:
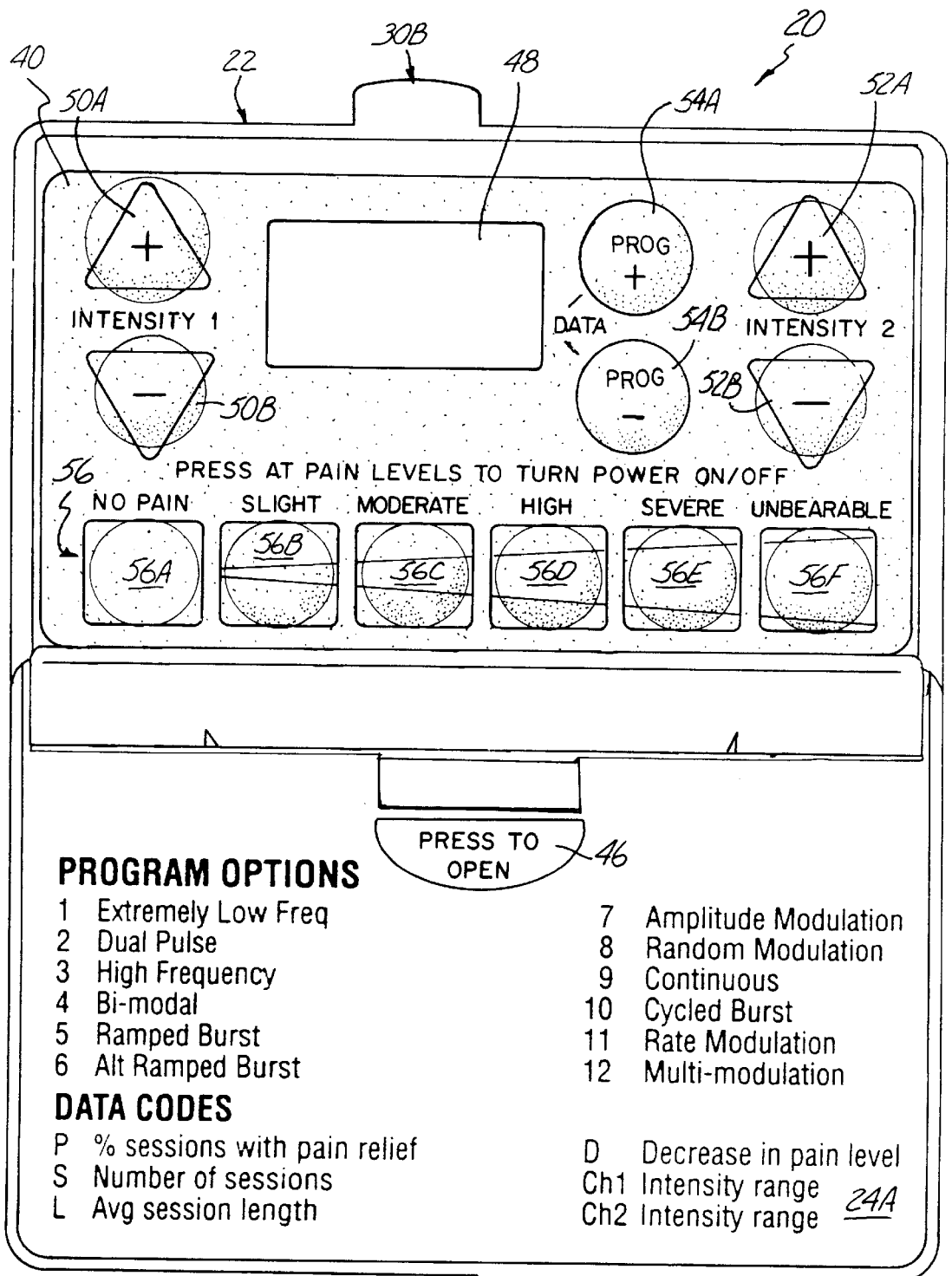
FIG. 4 is a front view of the control panel and the inside surface of the cover with the TENS device in the second open position.

As shown in general in FIGS. 1B and 1C, and in more detail in FIG. 4, control panel 40 includes display 48, channel 1 intensity control inputs 50A and 50B, channel 2 intensity control inputs 52A and 52B, pre-programmed (PPR) selection inputs 54A and 54B, and electronic pain intensity scale 56 (with inputs 56A–56F).

Display 48 allows the patient to view inputted data, current intensity settings, and treatment results. Display 48 also allows the clinician to retrieve data concerning the effectiveness of a patient's treatment.

The channel 1 intensity control inputs 50A and 50B and channel 2 intensity control inputs 52A and 52B allow the patient to regulate the intensity of the treatment being administered. In the preferred embodiment, the channel 1 intensity control inputs 50A and 50B and channel 2 intensity control inputs 52A and 52B are labeled "Intensity". Inputs 50A and 52A are labeled with a "+" denoting an increase in intensity, while inputs 50B and 52B are labeled with a "−" denoting a decrease in intensity.

The (PPR) selection inputs 54A and 54B are designed to allow the patient to select from a number of pre-programmed treatment regimens which are listed on inside surface 24A of cover 24 as "Program Options". In the preferred embodiment, the pre-programmed regimen selection inputs 54A and 54B are labeled "PROG +" and "PROG −", respectively. The PROG +input 54A allows the patient to scroll forward through the list of regimens, and PROG −input 54B allows the patient to scroll backwards.

By pressing both of the PROG +and PROG −selection inputs 54A and 54B simultaneously during power up, the clinician is able to access the data menu. The data menu provides the clinician with information related to the patient's treatment such as number of sessions, decrease in pain relief, percent of sessions with pain relief, average session length, channel 1 intensity range, and channel 2 intensity range. The data menu is listed on inside surface 24A of cover 24 as "Data Codes".

Electronic pain intensity scale 56 is preferably formed by an array of membrane switch inputs 56A–56F. The different areas of scale 56 are labelled to represent the different levels of pain inputted by the patient. Each area is associated with one of the plurality of inputs 56A–56F. Each input 56A–56F represents a different level of pain. In the preferred embodiment, scale 56 ranges from "No Pain" input 56A to "Slight" input 56B, to "Moderate" input 56C, to "High" input 56D, to "Severe" input 56E, to "Unbearable" input 56F. Therefore, the plurality of inputs 56A–56F, from left to right, represent increasing levels of perceived pain. As will later be described, depending upon which of the plurality of indicator inputs is selected, pain data is produced and stored.

Figure 5:
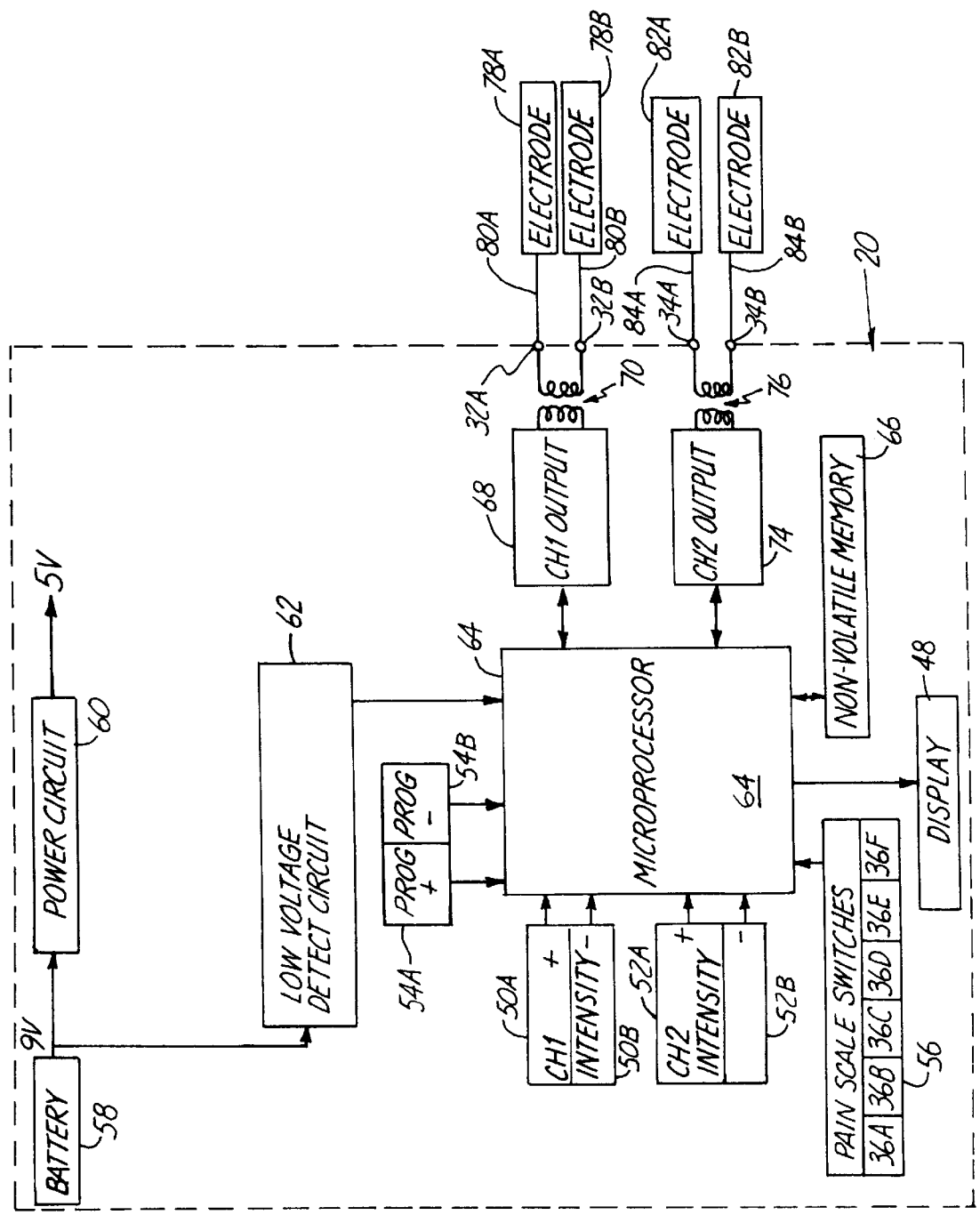
FIG. 5 is an electrical block diagram of the TENS device.

FIG. 5 is a block diagram of TENS device 20, which provides further detail of the inner components. TENS device 20 includes display 48, channel 1 intensity control inputs 50A and 50B, channel 2 intensity control inputs 52A and 52B, PROG selection inputs 54A and 54B, electronic pain intensity scale inputs 56A–56F, battery 58, power circuit 60, low voltage detect circuit 62, microprocessor 64, non-volatile memory 66, channel 1 output driver 68, channel 1 output transformer 70, channel 1 output terminals 32A and 32B, channel 2 output driver 74, channel 2 output transformer 76, and channel 2 output terminals 34A and 34B. TENS electrodes 78A and 78B are connected, through lead wires 80A and 80B, to channel 1 output terminals 32A and 32B, respectively. Similarly, TENS electrodes 82A and 82B are connected, through lead wires 84A and 84B, to channel 2 output terminals 34A and 34B.

Before a treatment session can begin, the patient must indicate his or her present level of perceived pain on the electronic pain intensity scale 56. In the preferred embodiment, the patient has six choices (inputs 56A–56F) to aid in subjectively assessing his or her pain levels. These choices range from "No Pain" to "Unbearable". The patient enters his or her perceived level of pain by pressing an appropriate location on the electronic pain intensity scale 56. Device 20 is normally powered up, but the microcontroller 64 is maintained in a stop mode to minimize power consumption. When any input (56A–56F) on scale 56 is pressed, a signal is sent to microprocessor 64. The signal activates microprocessor 64 and pain level data from the electronic pain intensity scale 56 is read and stored in memory 66 by microprocessor 64. The microprocessor 64 also stores the current time, which is maintained by the real time clock within microprocessor 64. After an initial pain level has been entered, treatment can begin. The patient selects one of the pre-programmed regimens by scrolling through the list of pre-programmed regimens using the PROG selection inputs 54A and 54B and viewing the selection on display 48. The patient uses channel 1 and channel 2 intensity control inputs 50A and 50B and 52A and 52B to adjust stimulation intensity for channels 1 and 2.

Microprocessor 64 controls channel 1 output driver 68 based upon the regimen selected through PROG selection inputs 54A and 54B and the intensity level selected through channel 1 intensity control inputs 50A and 50B. The output of channel 1 output driver 68 is supplied through transformer 70 to channel 1 output terminals 32A and 32B. TENS electrodes 78A and 78B are connected through lead wires 80A and 80B, respectively, to channel 1 output terminals 32A and 32B. TENS electrodes 78A and 78B are applied to the skin of the patient at the desired location to provide pain relief.

Similarly, microprocessor 64 controls channel 2 output driver 74 based upon the regimen selected and the intensity level selected through channel 2 intensity control inputs 52A and 52B. The output of channel 2 output driver 74 is supplied through transformer 76 to channel 2 output terminals 34A and 34B. TENS electrodes 82A and 82B are connected through lead wires 84A and 84B, respectively, to terminals 34A and 34B. The output of channel 2 output driver 74, therefore, is supplied to the patient through TENS electrodes 82A and 82B.

Microprocessor 64 stores the pain level input from one of pain level switches 56A–56F, together with the starting time when the pain scale switch was actuated, and the intensity setting for channel 1 and channel 2. If, during the course of a treatment session, the patient changes the intensity level, the new level and the time of change is recorded by microprocessor 64 in non-volatile memory 66. To end a treatment session, the patient again presses one of the pain scale switches 56A–56F. The patient has been instructed to press the input 56A–56F representing perceived pain at the time that the treatment is stopped. Upon receiving the second key press from pain scale switches 56A–56F, microprocessor 64 controls output drivers 68 and 74 to stop the treatment. In addition, microprocessor 64 records the final pain scale level (based upon which switch 56A–56F was pressed) together with the time. The recorded time can either be a real clock time, or can simply be a duration since the treatment session started.

TENS device 20 is able to aid the clinician in determining the effectiveness of the pain relief by displaying, on display 48, the percent of treatment sessions that recorded pain relief, and the degree of pain relief most often obtained. Device 20 also displays other helpful treatment assessment data such as the most frequently used intensity for each channel, the total number of treatment sessions, and the average length of each session. By using this information, the clinician can determine a patient's progress and whether the device was used appropriately. All of this information is based upon the pain scale input, time, and intensity data stored by microprocessor 64 in non-volatile memory 66 for each treatment session.

The data stored by microprocessor 64 in memory 66 (such as beginning pain level, ending pain level, duration and intensity) is also available for review by a clinician via display 48. This data can be in raw form, or microprocessor 64 will provide analysis of the data. The data or analyzed information is displayed by microprocessor 64 on display 48 when PROG + and PROG inputs 52A and 52B are pressed simultaneously.

TENS device 20 allows real time measurement of subjective perceptions or sensations and provides invaluable data for determining the effectiveness of a pain treatment. Device 20 is easy to use and allows measurements to be made in the real world of the patient i.e., in the home or at work. Further, device 20 forces the patient to consistently enter pain data, as the TENS treatment is only activated and deactivated upon entry of information on pain scale 56. The information output from device 20 can be used in a wide variety of applications and can provide a statistical correlation for evaluation a pain treatment or the consistency of the patient's response. Device 20 can automatically calculate, statistical parameters, such as a trend of the patients's pain and a histogram of the patients's pain levels grouped daily, weekly, or monthly.

Although the present invention has been described with reference to preferred embodiments, workers skilled in the art will recognize that changes may be made in form and detail without departing from the scope of the invention.

For example, the pain scale inputs with indicator zones labelled "No pain", "Slight", "Moderate", "High", "Severe", and "Unbearable" are also used advantageously in a device which includes a microprocessor and non-volatile memory, but does not include TENS outputs. That device can be used to record effectiveness of various pain treatments (such as medicinal treatments and non-medicinal treatments, including TENS).

What is claimed is:

1. A transcutaneous electrical nerve stimulation (TENS) device which is connected to TENS electrodes applied to a patient, which is worn by a patient and which allows the patient to control pain treatment while storing information used to evaluate the effectiveness of the pain treatment: the TENS device comprising:

a case;

a control panel including a display and a plurality of inputs, the control panel being mounted on the case wherein the plurality of inputs include intensity control inputs which allow the patient to regulate intensity of treatment being administered, pre-programmed selection inputs which allow the patient to select from a number of pre-programmed treatment regimens, and a pain intensity scale which allows the patient to input a level of perceived pain;

a plurality of output terminals at a surface of the case for connection to TENS electrodes;

electrical circuitry housed within the case and connected to the control panel, the inputs and the output terminals for controlling electrical stimulation supplied to the output terminals based upon a regimen and an intensity selected, and for storing data relating to pain levels;

a cover pivotally connected to the case;

a clip on the cover for attaching the cover to a patient's clothing so that the cover is generally vertical;

a latch for holding the case in a closed position adjacent the cover with the control panel generally vertical and located between the case and the cover, the latch being releasable to allow the case to pivot to a first open position in which the control panel is generally horizontal and is viewable and accessible by the patient; and a stop element on the case which engages the cover to define the first open position.

2. The TENS device of claim 1, wherein the cover has a flexible portion which, when flexed, does not engage the stop element to allow the case to pivot to a second open position beyond the first open position.

3. The TENS device of claim 1 wherein the latch comprises a pair of flexible fingers which extend from the cover to engage the case.

4. The TENS device of claim 1 and further comprising:

a first tab on the cover; and second tab on the case, the first and second tabs positioned so that opposite forces applied to the tabs cause the case to be released from the latch.

* * * * *